US012575850B2

(12) United States Patent
Heiliger

(10) Patent No.: US 12,575,850 B2
(45) Date of Patent: Mar. 17, 2026

(54) ARTICULATING ULTRASONIC SURGICAL INSTRUMENTS AND SYSTEMS

(71) Applicant: Covidien LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 517 days.

(21) Appl. No.: 17/799,197

(22) PCT Filed: Feb. 5, 2021

(86) PCT No.: PCT/US2021/016724

§ 371 (c)(1),
(2) Date: Aug. 11, 2022

(87) PCT Pub. No.: WO2021/178103

PCT Pub. Date: Sep. 10, 2021

(65) Prior Publication Data

US 2023/0074601 A1     Mar. 9, 2023

Related U.S. Application Data

(60) Provisional application No. 62/984,050, filed on Mar. 2, 2020.

(51) Int. Cl.
| | |
|---|---|
| *A61B 17/32* | (2006.01) |
| *A61B 17/22* | (2006.01) |

(52) U.S. Cl.
CPC ................. *A61B 17/320092* (2013.01); *A61B 2017/22015* (2013.01)

(58) Field of Classification Search
CPC .. A61B 17/320092; A61B 2017/22015; A61B 2017/22018; A61B 2017/2927;

(Continued)

(56) References Cited

U.S. PATENT DOCUMENTS

| | | | |
|---|---|---|---|
| 5,792,135 | A | 8/1998 | Madhani et al. |
| 5,897,523 | A | 4/1999 | Wright et al. |

(Continued)

FOREIGN PATENT DOCUMENTS

| | | |
|---|---|---|
| WO | 2016168549 A1 | 10/2016 |

OTHER PUBLICATIONS

Communication Pursuant to Article 94(3) EPC issued in corresponding European Application No. 21 709 234.5 dated May 6, 2024, 4 pages.

(Continued)

*Primary Examiner* — Tan-Uyen T Ho
*Assistant Examiner* — Bridget E. Rabaglia

(57) ABSTRACT

An ultrasonic surgical instrument includes an ultrasonic transducer and an ultrasonic waveguide coupled to the ultrasonic transducer and extending therefrom. The ultrasonic waveguide includes a proximal body portion coupled to and extending distally from the ultrasonic transducer and defining a longitudinal axis. The ultrasonic waveguide further includes a distal body portion defining a blade, and a plurality of spheres of material arranged in a series. The plurality of spheres of material extend between and interconnect the proximal body portion and the distal body portion. At least one sphere of material of the plurality of spheres of material is configured to articulate relative to at least one other sphere of material of the plurality of spheres of material to thereby articulate the distal body portion from an aligned orientation on the longitudinal axis to an articulated orientation angled off the longitudinal axis.

19 Claims, 8 Drawing Sheets

(58) Field of Classification Search

CPC ......... A61B 2017/320071; A61B 2017/00314; A61B 2017/320094; A61B 2017/320095; A61B 17/320068; A61B 18/1445; A61B 2017/320093; A61B 2017/00477; A61B 2017/320069; A61B 2018/0063; A61B 2018/00601; A61B 2018/00607; A61B 17/2202; A61B 17/22012; A61B 17/22004; A61B 2017/22007; A61B 2017/22005; A61B 2017/22008; A61B 2017/22009; A61B 2017/22011; A61B 2017/22014; A61B 2017/22024; A61B 2018/00994; A61B 2018/1455; A61B 2017/320088

See application file for complete search history.

(56) References Cited

U.S. PATENT DOCUMENTS

| | | | |
|---|---|---|---|
| 5,940,347 | A * | 8/1999 | Raida .................... G10K 11/24 367/138 |
| 6,783,524 | B2 * | 8/2004 | Anderson .............. A61B 34/30 606/1 |
| 7,135,030 | B2 | 11/2006 | Schwemberger et al. |
| 10,172,636 | B2 | 1/2019 | Stulen et al. |
| 10,226,274 | B2 | 3/2019 | Worrell et al. |
| 10,258,363 | B2 | 4/2019 | Worrell et al. |
| 10,335,182 | B2 | 7/2019 | Stulen et al. |
| 10,405,876 | B2 | 9/2019 | Boudreaux |
| 10,413,316 | B2 | 9/2019 | Lyons |
| 10,492,819 | B2 | 12/2019 | Hibner |
| 10,575,836 | B2 | 3/2020 | Hibner et al. |
| 10,912,581 | B2 | 2/2021 | Stulen et al. |
| 10,925,630 | B2 | 2/2021 | Cuti et al. |
| 10,987,123 | B2 | 4/2021 | Weir et al. |
| 11,337,717 | B2 | 5/2022 | Lyons |
| 2004/0024402 | A1 | 2/2004 | Nita |
| 2006/0058825 | A1 * | 3/2006 | Ogura ............ A61B 17/320092 606/169 |
| 2006/0190034 | A1 | 8/2006 | Nishizawa et al. |
| 2008/0214967 | A1 | 9/2008 | Aranyi et al. |
| 2009/0163948 | A1 | 6/2009 | Sunaoshi et al. |
| 2013/0012959 | A1 | 1/2013 | Jinno |
| 2013/0140835 | A1 | 6/2013 | Stefanchik |
| 2014/0005701 | A1 * | 1/2014 | Olson .................. A61B 17/295 606/206 |
| 2014/0005702 | A1 | 1/2014 | Timm et al. |
| 2014/0276931 | A1 | 9/2014 | Parihar et al. |
| 2014/0309562 | A1 | 10/2014 | Ito |
| 2014/0350570 | A1 | 11/2014 | Lee |
| 2015/0080924 | A1 | 3/2015 | Stulen et al. |
| 2015/0320437 | A1 * | 11/2015 | Worrell ......... A61B 17/320068 606/169 |
| 2016/0106431 | A1 * | 4/2016 | Shelton, IV ......... A61B 17/072 227/180.1 |
| 2016/0302812 | A1 | 10/2016 | Monroe et al. |
| 2017/0172607 | A1 * | 6/2017 | Houser ......... A61B 17/320092 |
| 2019/0021752 | A1 * | 1/2019 | Boudreaux .... A61B 17/320068 |
| 2019/0021756 | A1 | 1/2019 | Boudreaux |
| 2019/0133635 | A1 | 5/2019 | Stulen et al. |
| 2019/0216493 | A1 | 7/2019 | Worrell et al. |
| 2019/0247083 | A1 | 8/2019 | Worrell et al. |
| 2019/0290318 | A1 | 9/2019 | Boudreaux |
| 2019/0321068 | A1 | 10/2019 | Hibner et al. |
| 2019/0321069 | A1 | 10/2019 | Hibner |
| 2019/0321070 | A1 | 10/2019 | Boudreaux |
| 2019/0380735 | A1 | 12/2019 | Cuti et al. |
| 2020/0229833 | A1 | 7/2020 | Vakharia et al. |
| 2020/0229834 | A1 | 7/2020 | Olson et al. |
| 2020/0237397 | A1 | 7/2020 | Boudreaux |
| 2020/0237399 | A1 | 7/2020 | Stulen et al. |
| 2021/0204941 | A1 * | 7/2021 | Dewaele ................ A61B 34/71 |
| 2021/0353324 | A1 | 11/2021 | Fagan et al. |
| 2021/0353325 | A1 | 11/2021 | Fagan et al. |

OTHER PUBLICATIONS

International Search Report and Written Opinion received for PCT Patent Application No. PCT/US2021/016724, mailed on May 25, 2021, 10 pages.

* cited by examiner

ARTICULATING ULTRASONIC SURGICAL INSTRUMENTS AND SYSTEMS

CROSS-REFERENCE TO RELATED APPLICATIONS

This application is a 371 National Stage Application of International Application No. PCT/US2021/016724, filed Feb. 5, 2021, which claims benefit of U.S. Provisional Patent Application No. 62/984,050, filed Mar. 2, 2020, the entire contents of each of which is hereby incorporated herein by reference.

FIELD

The present disclosure relates to surgical instruments and systems and, more particularly, to articulating ultrasonic surgical instruments and systems.

BACKGROUND

Ultrasonic surgical instruments and systems utilize ultrasonic energy, i.e., ultrasonic vibrations, to treat tissue. More specifically, a typical ultrasonic surgical instrument or system includes a transducer configured to produce mechanical vibration energy at ultrasonic frequencies that is transmitted along a waveguide to an ultrasonic end effector configured to treat, e.g., coagulate, cauterize, fuse, seal, cut, desiccate, fulgurate, or otherwise treat tissue.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

As used herein, the term "distal" refers to the portion that is being described which is further from a user, while the term "proximal" refers to the portion that is being described which is closer to a user. Further, to the extent consistent, any or all of the aspects detailed herein may be used in conjunction with any or all of the other aspects detailed herein.

Provided in accordance with the present disclosure is an ultrasonic surgical instrument including an ultrasonic transducer and an ultrasonic waveguide coupled to the ultrasonic transducer and extending therefrom. The ultrasonic waveguide includes a proximal body portion, a distal body portion defining a blade, and a plurality of spheres of material. The proximal body portion is coupled to and extends distally from the ultrasonic transducer. The proximal body portion defines a longitudinal axis. The plurality of spheres of material is arranged in a series. The plurality of spheres of material extend between and interconnect the proximal body portion and the distal body portion. At least one sphere of material of the plurality of spheres of material is configured to articulate relative to at least one other sphere of material of the plurality of spheres of material to thereby articulate the distal body portion from an aligned orientation on the longitudinal axis to an articulated orientation angled off the longitudinal axis.

In an aspect of the present disclosure, a flexible sleeve is disposed about the plurality of spheres of material and configured to maintain the plurality of spheres of material in the series with each sphere of material in contact with any adjacent spheres of material. In such aspects, the flexible sleeve may further be configured to maintain the plurality of spheres of material under compression. Alternatively or additionally, the flexible sleeve may extend proximally to be disposed about a portion of the proximal body portion and/or distally to be disposed about a portion of the distal body portion.

In another aspect of the present disclosure, in the articulated orientation, the distal body portion is disposed at an angle of about 45 degrees to about 90 degrees relative to the longitudinal axis.

In yet another aspect of the present disclosure, the ultrasonic surgical instrument further includes an elongated shaft surrounding at least a portion of the proximal body portion of the ultrasonic waveguide, a support shaft surrounding at least a portion of the distal body portion of the ultrasonic waveguide, and an articulating portion extending between and interconnecting the elongated shaft and the support shaft. The plurality of spheres of material extend through the articulating portion.

In still another aspect of the present disclosure, the ultrasonic surgical instrument further includes a jaw pivotably coupled to the distal support shaft and configured to pivot relative to the blade between an open position and a clamping position to enable clamping of tissue between the jaw and the blade.

In still yet another aspect of the present disclosure, the ultrasonic surgical instrument further includes a handle assembly. The elongated shaft and proximal body portion of the ultrasonic waveguide extend distally from the handle assembly. The handle assembly supports the ultrasonic transducer thereon.

In another aspect of the present disclosure, a robotic arm of a robotic surgical system is provided wherein the elongated shaft and proximal body portion of the ultrasonic waveguide extend distally from the robotic arm. In such aspects, the robotic arm may support the ultrasonic transducer thereon.

In yet another aspect of the present disclosure, at least one sphere of material of the plurality of spheres of material is configured to articulate in a first direction and at least one sphere of material of the plurality of spheres of material is configured to articulate in a second, different direction. The second direction may be perpendicular to the first direction.

A surgical ultrasonic waveguide assembly provided in accordance with aspects of the present disclosure includes a proximal body portion configured to connect to an ultrasonic transducer and defining a longitudinal axis, a distal body portion defining a blade, and a plurality of spheres of material arranged in a series. The plurality of spheres of material extends between and interconnects the proximal body portion and the distal body portion. At least one sphere of material of the plurality of spheres of material is configured to articulate relative to at least one other sphere of material of the plurality of spheres of material to thereby articulate the distal body portion from an aligned orientation on the longitudinal axis to an articulated orientation angled off the longitudinal axis. A flexible sleeve is disposed about the plurality of spheres of material and configured to maintain the plurality of spheres of material in the series with each sphere of material in contact with any adjacent spheres of material.

In an aspect of the present disclosure, the proximal body portion is a solid rod of material.

In another aspect of the present disclosure, the distal body portion is a solid rod of material.

In still another aspect of the present disclosure, each of the spheres of material is a solid sphere of material.

In yet another aspect of the present disclosure, each of the spheres of material is formed from stainless steel.

In still yet another aspect of the present disclosure, the blade is curved in at least one direction and/or tapered in at least one dimension in a proximal-to-distal direction.

In another aspect of the present disclosure, the flexible sleeve is further configured to maintain the plurality of spheres of material under compression. Additionally or alternatively, the flexible sleeve extends proximally to be disposed about a portion of the proximal body portion and/or distally to be disposed about a portion of the distal body portion.

In another aspect of the present disclosure, in the articulated orientation, the distal body portion is disposed at an angle of about 45 degrees to about 90 degrees relative to the longitudinal axis.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
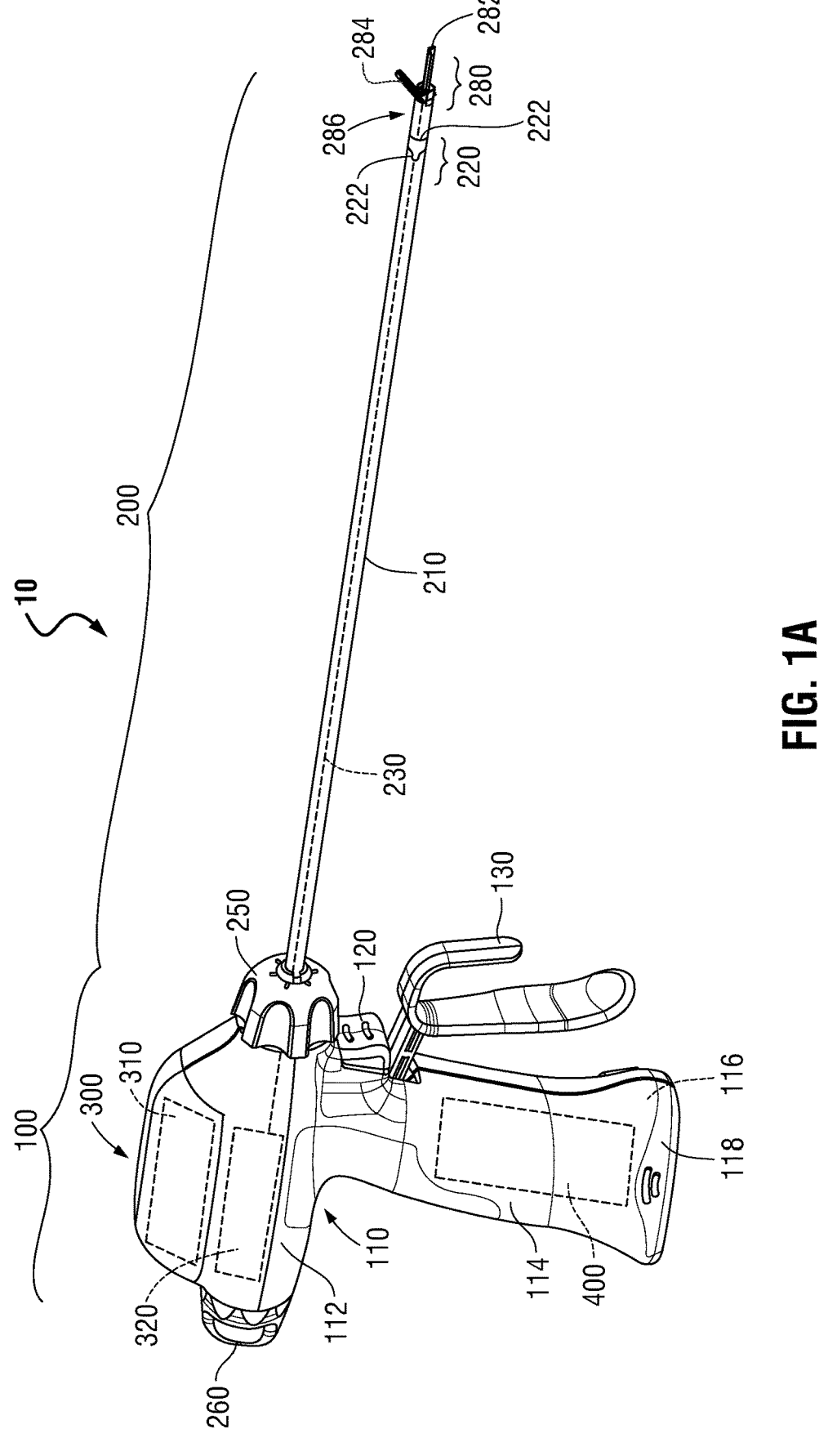
FIG. 1A is a perspective view of a hand-held articulating ultrasonic surgical instrument provided in accordance with the present disclosure, wherein the elongated assembly is disposed in an un-articulated position.
Figure 1B:
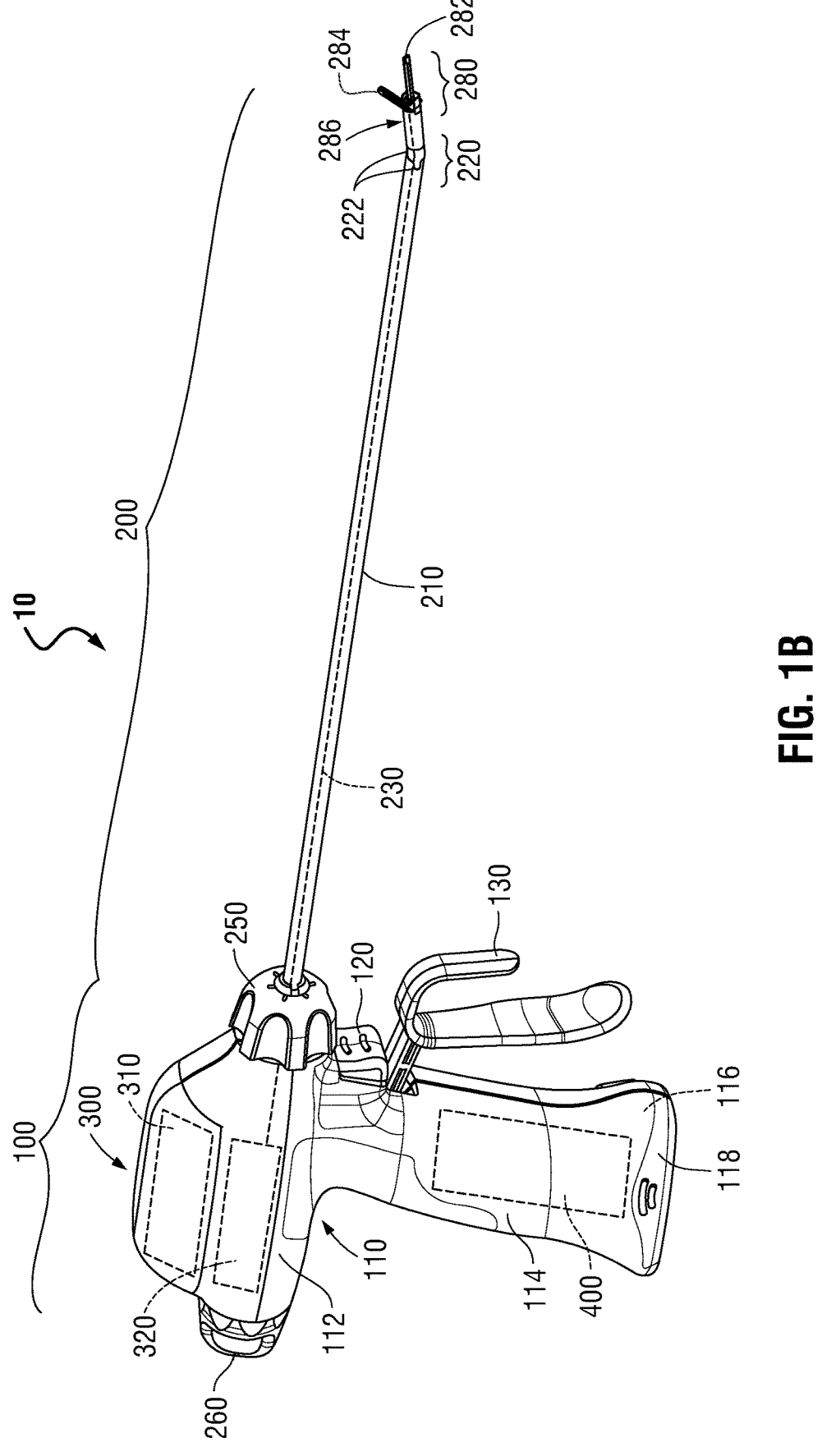
FIG. 1B is a perspective view of the hand-held articulating ultrasonic surgical instrument of FIG. 1A, wherein the elongated assembly is disposed in an articulated position.

Referring generally to FIGS. 1A and 1B, an embodiment of a hand-held ultrasonic surgical instrument exemplifying the aspects and features of the present disclosure is shown generally identified by reference numeral 10. For the purposes herein, hand-held ultrasonic surgical instrument 10 is generally described. Aspects and features of hand-held ultrasonic surgical instrument 10 not germane to the understanding of the present disclosure are omitted to avoid obscuring the aspects and features of the present disclosure in unnecessary detail.

Hand-held ultrasonic surgical instrument 10 generally includes a handle assembly 100 and an elongated assembly 200 extending distally from handle assembly 100. Handle assembly 100 includes a housing 110 defining a body portion 112 and a fixed handle portion 114. Handle assembly 100 further includes an activation button 120 and a clamp trigger 130.

Body portion 112 of housing 110 is configured to support an ultrasonic transducer and generator assembly ("TAG") 300 including a generator assembly 310 and an ultrasonic transducer assembly 320. TAG 300 may be permanently engaged with body portion 112 of housing 110 or removable therefrom. Alternatively, generator assembly 310 may be remotely disposed and coupled to ultrasonic surgical instrument 10 by way of a surgical cable.

Fixed handle portion 114 of housing 110 defines a compartment 116 configured to receive a battery assembly 400 and a door 118 configured to enclose compartment 116. An electrical connection assembly (not shown) is disposed within housing 110 of handle assembly 100 and serves to electrically couple activation button 120, generator assembly 310 of TAG 300, and battery assembly 400 with one another when TAG 300 is supported on body portion 112 of housing 110 and battery assembly 400 is disposed within compartment 116 of fixed handle portion 114 of housing 110, thus enabling activation of ultrasonic surgical instrument 10 in response to depression of activation button 120. In embodiments where generator assembly 310 is remote from ultrasonic surgical instrument 10, battery assembly 400 and the configuration of fixed handle portion 114 for receiving battery assembly 400 need not be provided, as the remote generator assembly 310 may be powered by a standard wall outlet or other remote power source.

Figures 3, 4:
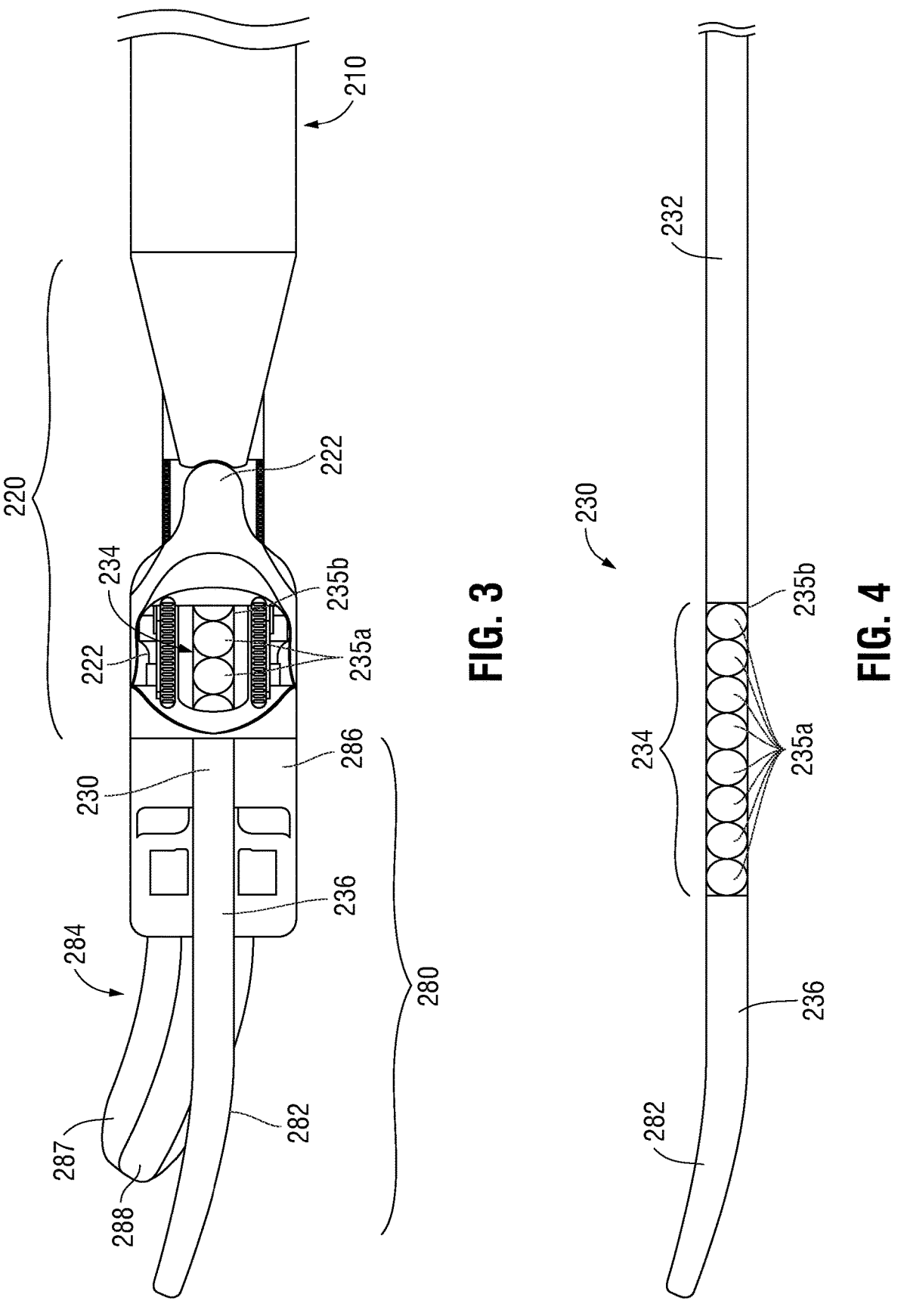
FIG. 3 is an enlarged, bottom view of a distal end portion of the articulating ultrasonic surgical instrument of FIG. 1, disposed in a linear orientation.
FIG. 4 is an enlarged, bottom view of a distal end portion of a waveguide of the articulating ultrasonic surgical instrument of FIG. 1, disposed in the linear orientation.
Figure 6:
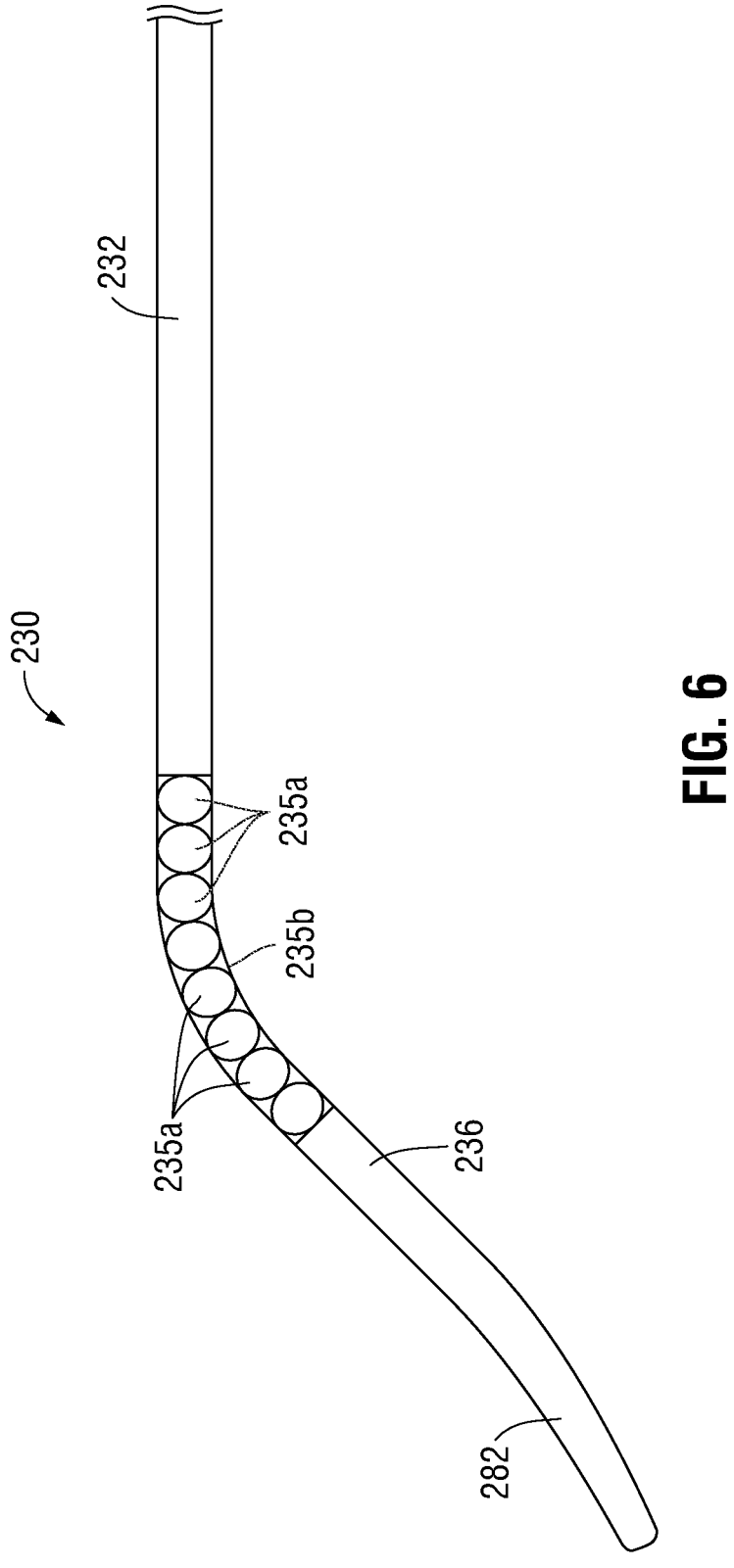
FIG. 6 is an enlarged, bottom view of the distal end portion of the waveguide of the articulating ultrasonic surgical instrument of FIG. 1, disposed in the articulated orientation.

Elongated assembly 200 of ultrasonic surgical instrument 10 includes an elongated shaft 210, an articulation section 220, a waveguide 230 (see FIGS. 4 and 6) extending through elongated shaft 210 and articulation section 220, a drive assembly (not shown), an articulation assembly (not shown), a rotation knob 250, and an end effector 280 including a blade 282, a jaw 284, and a support shaft 286.

Referring still to FIGS. 1A and 1B, elongated shaft 210 extends distally from body portion 112 of housing 110. Articulation section 220 is coupled to and extends distally from elongated shaft 210 and support shaft 286 of end effector 280 is coupled to and extends distally from articulation section 220. In this manner, articulation of articulation section 220 relative to elongated shaft 210 and housing 110 articulates end effector 280 relative to elongated shaft 210 and housing 110. Articulation section 220 may include one or more articulation components 222, e.g., articulation joint(s), articulation linkage(s), flexible portion(s), etc., coupled between elongated shaft 210 and support shaft 286 of end effector 280 to enable articulation of support shaft 286 and end effector 280 relative to elongated shaft 210 and housing 110 in at least one plane, e.g., pitch articulation and/or yaw articulation. In embodiments, articulation section 220 is configured to enable articulation in two substantially perpendicular planes, e.g., both pitch articulation and yaw articulation. This may be accomplished by providing two articulation joints 222 disposed in substantially perpendicular orientation relative to one another or in any other suitable manner.

Figure 5:
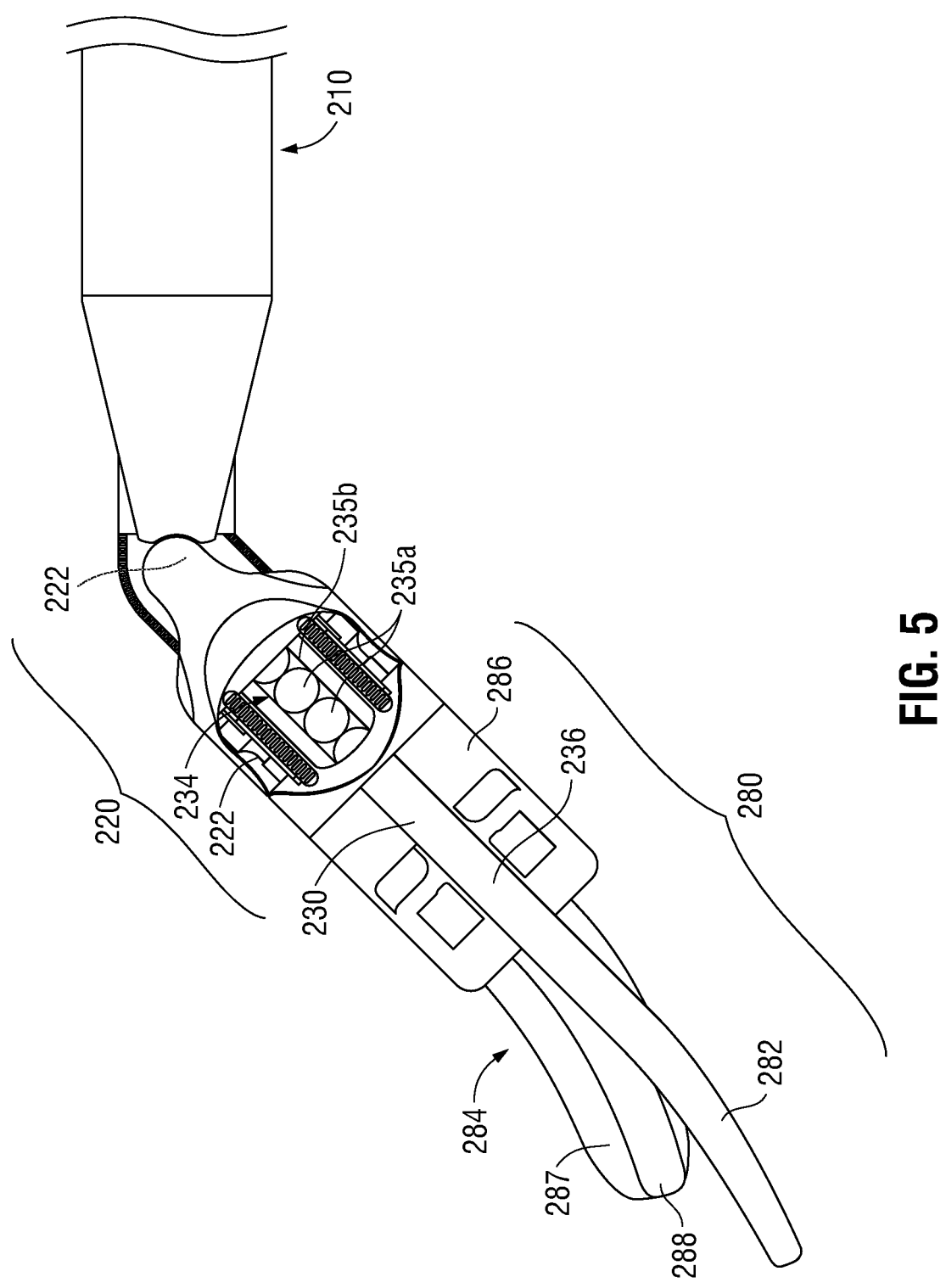
FIG. 5 is an enlarged, bottom view of the distal end portion of the articulating ultrasonic surgical instrument of FIG. 1, disposed in an articulated orientation.

Jaw 284 is pivotably mounted on a distal end portion of support shaft 286 and the drive assembly operably couples clamp trigger 130 of handle assembly 100 with jaw 284 of end effector 280 such that clamp trigger 130 is selectively actuatable to pivot jaw 284 relative to support shaft 286 and blade 282 of end effector 280 between an open position and a clamping position for clamping tissue between jaw 284 and blade 282. The drive assembly may include a drive shaft, drive sleeve, drive cables, and/or other suitable components extending through handle assembly 100, elongated shaft 210, articulation section 220, and support shaft 286 to operably couple clamp trigger 130 with jaw 284 to enable pivoting of jaw 284 between the open and clamping positions regardless of the articulation of articulation section 220. Jaw 284 includes a more-rigid structural body 287 which is pivotably mounted on a distal end portion of support shaft 286, and a more-compliant jaw liner 288 secured to the more-rigid structural body 287 and positioned to oppose blade 282 to enable clamping of tissue therebetween (see also FIGS. 3 and 5).

Rotation knob 250 is rotatable in either direction to rotate elongated assembly 200 in either direction relative to handle assembly 100. The articulation assembly may include gears, pulleys, tension cables, etc., that operably couple an articulation knob 260 disposed on handle assembly 100 with the one or more articulation components 222 of articulation section 220 such that rotation of articulation knob 260 manipulates articulating section 220 to thereby articulate end effector 280 relative to elongated shaft 210. Alternatively, articulation knob 260 may be operably coupled to support shaft 286 to induce articulating motion. Additional articulation actuators and/or other suitable articulation actuators are also contemplated.

Ultrasonic transducer assembly 320 includes a plurality of piezoelectric elements or other suitable transducer component(s) configured to convert an electrical drive signal into ultrasonic vibration energy for transmission along waveguide 230 (see FIGS. 4 and 6) to blade 282. Generator assembly 310, powered by battery 400 (or another power source), is configured to generate the electrical drive signal and provide the same to ultrasonic transducer assembly 320. Ultrasonic transducer assembly 320 may be configured to generate any suitable mode of ultrasonic vibration energy for transmission to proximal body portion 232 of waveguide 230 (see FIGS. 4 and 6). More specifically, ultrasonic transducer assembly 320 may be configured to produce a longitudinal mode of ultrasonic vibration energy, wherein longitudinal ultrasonic vibrations in directions coaxial or parallel with the longitudinal axis of proximal body portion 232 of waveguide 230 are generated and transmitted to proximal body portion 232 of waveguide 230 (see FIGS. 4 and 6).

Figure 2:
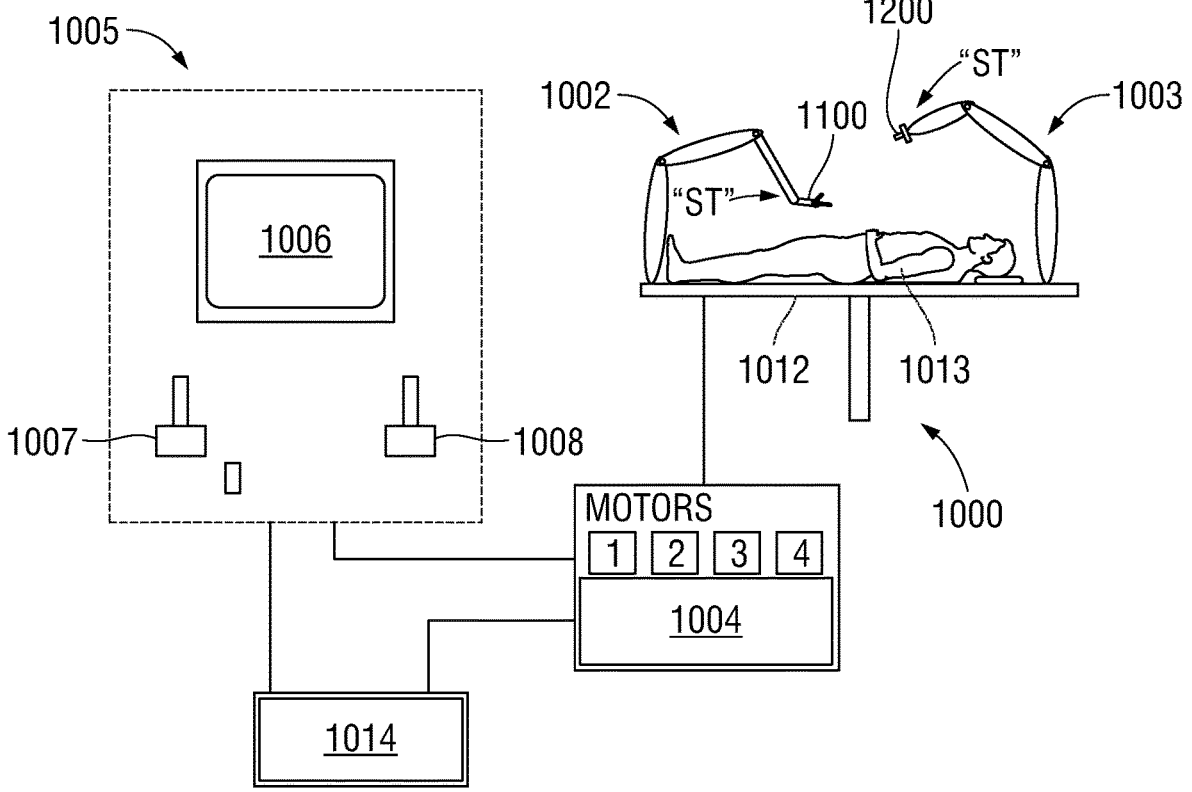
FIG. 2 is a schematic illustration of a robotic surgical system configured for use with an articulating ultrasonic surgical instrument, provided in accordance with the present disclosure.

Referring generally to FIG. 2, an embodiment of a robotic surgical system exemplifying the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003. Robotic surgical system 1000 may be configured for use on a patient 1013 lying on a patient table 1012 to be treated in a minimally invasive or other suitable manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, to which may be attached, for example, a surgical tool "ST" supporting an end effector assembly 1100, 1200. End effector assembly 1100 may be configured as an articulating ultrasonic surgical instrument similarly as detailed above with respect to instrument 10 (FIGS. 1A and 1B) except that robot arm 1002 replaces handle assembly 100 (FIGS. 1A and 1B). End effector 1200 may be any other suitable surgical end effector, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, and, thus, the surgical tools "ST" (including end effectors 1100, 1200) execute a desired movement and/or function according to a corresponding input from manual input devices 1007, 1008, respectively. Control device 1004 may also be configured in such a way that it regulates the movement of robot arms 1002, 1003 and/or of the motors.

With reference to FIGS. 3-6, waveguide 230, as noted above, extends through elongated shaft 210 and articulation section 220. Waveguide 230, more specifically, defines a proximal body portion 232, an articulation portion 234, and a distal body portion 236 defining a blade 282 (e.g., wherein blade 282 forms a portion of or the entirety of distal body portion 236).

Proximal body portion 232 of waveguide 230 is formed as a rod of material, e.g., stainless steel, titanium, or other suitable material capable of transmitting ultrasonic energy therealong. Proximal body portion 232 may be formed as a single, integral component or may include plural components separately formed and subsequently joined to one another (permanently or releasably) to form proximal body portion 232 of waveguide 230. Proximal body portion 232 of waveguide 230 is substantially rigid in that proximal body portion 232 is not configured to articulate during use.

A portion of proximal body portion 232 extends proximally into handle assembly 100 (FIGS. 1A and 1B) to connect to ultrasonic transducer assembly 320 of TAG 300. This connection may be releasable or permanent and may be made via threaded engagement (e.g., via a threaded connector (not shown) disposed at a proximal end of proximal body portion 232 and configured to engage a threaded connector (not shown) of ultrasonic transducer assembly 320), latching, integral formation, permanent welding or other bonding, or in any other suitable manner. Proximal body portion 232 of waveguide 230 extends distally from handle assembly 100 through elongated shaft 210 of elongated assembly 200.

Continuing with reference to FIGS. 3-6, articulation portion 234 of waveguide 230 is formed from a plurality of spheres of material 235a, e.g., stainless steel, titanium, or other suitable material capable of transmitting ultrasonic energy therealong, arranged in a 1 by "N" series in a general longitudinal direction, wherein "N" is the number of spheres of material 235a, although other configurations are also contemplated. In embodiments, the number of spheres of material 235a may be at least 4, at least 6, or at least 8. In other embodiments, a single sphere or less than 4 spheres may be provided. The spheres of material 235a may be solid or, in other embodiments, may be hollow or partially hollow. A flexible sleeve 235b is disposed about the plurality of spheres of material 235a to maintain the 1 by "N" series, abutment between adjacent spheres of material 235a, abutment of a proximal-most sphere of material 235a with a distal end of proximal body portion 232 of waveguide 230, and abutment of a distal-most sphere of material 235a with a proximal end of distal body portion 236 under compression while still enabling articulation of the plurality of spheres of material 235a relative to one another. This compression enables transmission of ultrasonic energy from proximal body portion 232, along the plurality of spheres of material 235a, to distal body portion 236 for transmission to blade 282 regardless of the articulated orientation of the plurality of spheres of material 235a and/or distal body portion 236.

Articulation portion 234 is configured to be articulated between an aligned, linear orientation (FIGS. 3 and 4), wherein the plurality of spheres of material 235a are substantially aligned on a longitudinal axis of waveguide 230, and an articulated orientation (FIGS. 5 and 6), wherein at least one of the plurality of spheres of material 235a extends radially off the longitudinal axis of waveguide 230 at an angle relative thereto. The smooth, curved outer surfaces of the plurality of spheres of material 235a facilitate articulation of the spheres of material 235a relative to one another while maintaining contact with adjacent spheres of material 235a under compression. One or more of the plurality of spheres of material 235a may be configured, in the articulated orientation (FIGS. 5 and 6), to extend from the longitudinal axis of the waveguide 230 at an angle of about 45 degrees to about 90 degrees. In other embodiments, one or more of the plurality of spheres of material 235a may extend at an angle of less than 45 degrees or more than 90 degrees. The plurality of spheres of material 235a are not limited to one direction of articulation but may, in embodiments, be configured to articulate in two or more directions, e.g., first and second perpendicular directions to achieve pitch and yaw articulation.

Flexible sleeve 235b extends proximally from articulation portion 234 to at least partially overlap and surround a portion of proximal body portion 232 of waveguide 230, and extends distally from articulation portion 234 to at least partially overlap and surround a portion of distal body portion 236 of waveguide 230. In embodiments, flexible sleeve 235b extends about at least a majority of a length of proximal body portion 232 and/or distal body portion 236. In embodiments, flexible sleeve 235b extends about an entirety of proximal body portion 232 and/or distal body portion 236 (e.g., at least 90% of a length of proximal body portion 232 and/or distal body portion 236). Other configurations are also contemplated. Flexible sleeve 235b may be formed from any suitable material. As an alternative to or in addition to flexible sleeve 235b, other suitable internal and/or external support structures may be provided such as, for example, a support cage enclosing the plurality of spheres of material 235a, an internal central cable (e.g., spring loaded) extending though and joining the plurality of spheres of material 235a, and/or other suitable structures.

Referring still to FIGS. 3-6, articulation portion 234 of waveguide 230 extends through articulation section 220 (including the one or more articulation components 222 thereof) of elongated assembly 200 and is configured for passive articulation. In embodiments, articulation section 220 and articulation portion 234 defines substantially similar lengths (e.g., within 10% of one another), although other configurations are also contemplated. As a result of (any of) the above configuration(s), in response to articulation of articulating section 220, articulating portion 234 of waveguide is configured to articulate in a similar manner.

Distal body portion 236 of waveguide 230 extends distally from articulation portion 234 of waveguide 230 through support shaft 286 of elongated assembly 200 and defines blade 282 (e.g., wherein blade 282 forms a portion of or the entirety of distal body portion 236). Blade 282 is positioned to oppose jaw 284 to enable clamping of tissue therebetween.

Distal body portion 236 of waveguide 230 is formed as a rod of material, e.g., stainless steel, titanium, or other suitable material capable of transmitting ultrasonic energy therealong. Distal body portion 236 may be formed as a single, integral component or may include plural components separately formed and subsequently joined to one another (permanently or releasably) to form distal body portion 236 of waveguide 230. Distal body portion 236 of waveguide 230 is substantially rigid in that distal body portion 236 is not configured to articulate during use.

Blade 282 serves as the blade of end effector 280 and, as noted above, is defined by a portion or the entirety of distal body portion 236. Blade 282 may define a curved configuration wherein the directions of movement of jaw 284 between the open and clamping positions are perpendicular to the direction of curvature of blade 282. However, it is also contemplated that blade 282 define a straight configuration or that blade 282 curve towards or away from jaw 284, that is, where the directions of movement of jaw 284 between the open and clamping positions are coplanar or parallel to the direction of curvature of blade 282. Multiple curvatures of blade 282 (in the same or different directions) and/or combinations of curved and linear portions of blade 282 are also contemplated. Likewise, some portions or surfaces of blade 282 may be curved while others are not curved. Blade 282 may additionally or alternatively taper in width (a dimension perpendicular to the directions of movement of jaw 284 between the open and clamping positions) in a proximal-to-distal direction and/or in height (a dimension parallel or coplanar with the directions of movement of jaw 284 between the open and clamping positions) in a proximal-to-distal direction. Other configurations are also contemplated. The above features of blade 282 may be formed via removing material, bending, and/or otherwise manipulating at least a portion of the rod of material forming distal body portion 236, by joining components to one another, or in any other suitable manner.

With general reference to FIGS. 1A-6, in use, ultrasonic instrument 10 is advanced into a surgical site and manipulated such that end effector 280 is positioned with tissue to be treated disposed between jaw 284 and blade 282 with jaw 284 disposed in the open position. Alternatively, blade 282 may be positioned near tissue for clamp-less tissue treatment, e.g., dissection, plunging, scoring, etc. In order to better position end effector 280 relative to tissue to be treated, end effector 280 may be articulated relative to elongated shaft 210 about articulating section 230 of elongated assembly 200, as detailed above.

Where it is desired to clamp tissue, once tissue is positioned between jaw 284 and blade 282, clamp trigger 130 is squeezed towards fixed handle portion 114 from the unactuated position to the actuated position to pivot jaw 284 relative to blade 282 from the open position to the closed position to clamp tissue between jaw 284 and blade 282 and, more specifically, between jaw liner 288 of jaw 284 and blade 282. Blade 282 may then be activated, e.g., via depression of activation button 120, to supply ultrasonic energy from TAG 300, along waveguide 230, to blade 282 regardless of the articulated orientation of blade 282. The ultrasonic energy provided at blade 282 is used to treat, e.g., coagulate, cauterize, fuse, seal, cut, desiccate, fulgurate, etc., tissue clamped between jaw 284 and blade 282 or otherwise positioned near blade 282.

Figure 7A:
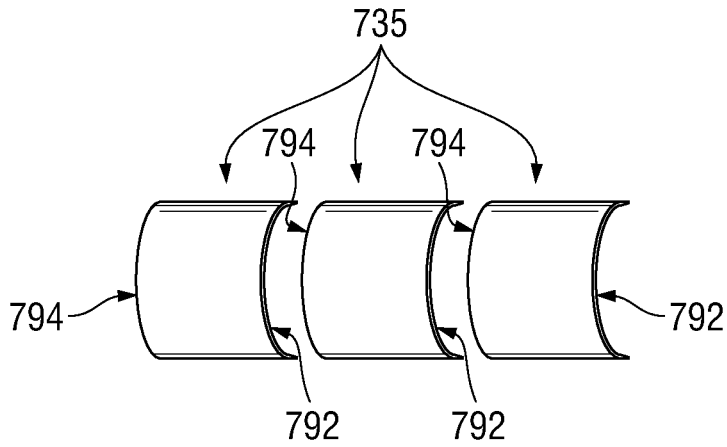
FIGS. 7A-7C illustrate exploded, aligned, and articulated views, respectively, of another configuration of an articulating portion of an ultrasonic waveguide in accordance with the present disclosure.
Figure 7B:
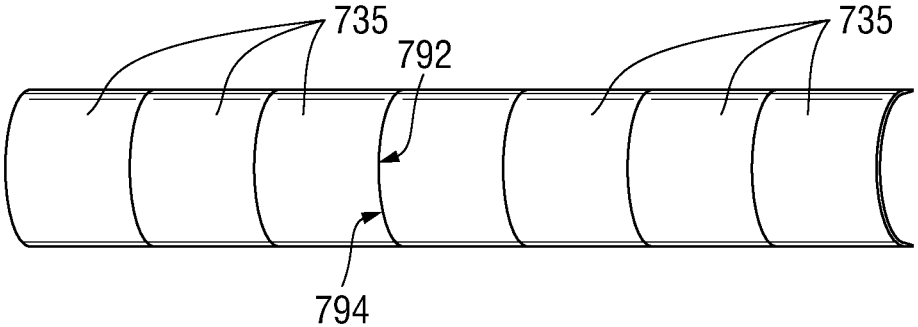
Figure 7C:
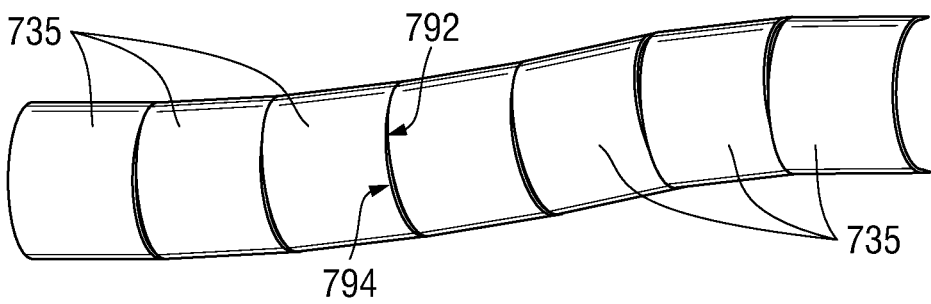

In embodiments, spheres of material 235a (FIGS. 3-6) need not be perfectly spherical but can have variation, e.g., plus or minus 10 percent from perfectly spherical, so long as the contacting surfaces between adjacent spheres of material 235a (FIGS. 3-6) are able to be maintained under compression while permitting relative articulation of the adjacent spheres of material 235a (FIGS. 3-6). Further, with reference to FIGS. 7A-7C and 8A-8C, in embodiments, some or all of the spheres of material 235a (FIGS. 3-6) may be replaced with other suitable components of material. For example, as illustrated in FIGS. 7A-7C, components of material 735 are not fully spherical but, instead, at least define opposing concave and convex spherical surface portions 792, 794. In this manner, the concave and convex spherical surface portions 792, 794 of adjacent pairs of components of material 735 are maintained in contact with one another under compression (and may be complementary or non-complementary with one another) while still permitting relative articulation between the adjacent components of material 735. In other embodiments, components of material 735 define opposing convex spherical surface portions 794 such that adjacent convex spherical surface portions 794 are maintained in contact with one another under compression while still permitting relative articulation between the adjacent components of material 735.

Figure 8A:
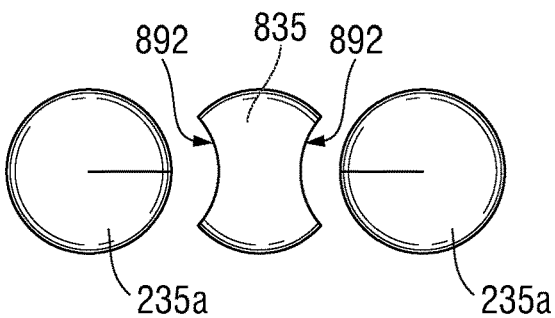
FIGS. 8A-8C illustrate exploded, aligned, and articulated views, respectively, of yet another configuration of an articulating portion of an ultrasonic waveguide in accordance with the present disclosure.
Figure 8B:
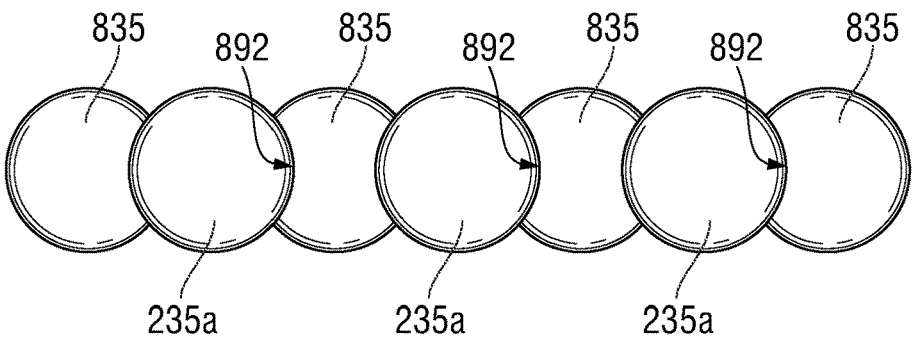
Figure 8C:
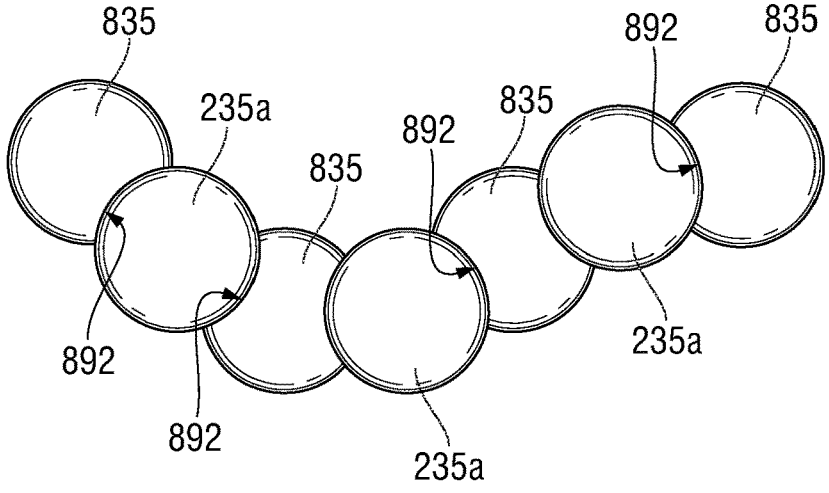

With reference to FIGS. 8A-8C, in embodiments, spheres of material 235a and components of material 835 are alternatingly disposed in series. Components of material 835 define opposed concave surface portions 892 that are configured to be maintained in contact with the spherical surface portions of adjacent spheres of material 235a under compression (and may be complementary or non-complementary with one another) while still permitting relative articulation between each adjacent pair of spheres of material 235a and components of material 735.

It should be understood that various aspects disclosed herein may be combined in different combinations than the combinations specifically presented in the description and accompanying drawings. Further, while several embodiments of the disclosure are presented in the description and accompanying drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
an ultrasonic transducer; and
an ultrasonic waveguide coupled to the ultrasonic transducer and extending therefrom, the ultrasonic waveguide including:
a proximal body portion coupled to and extending distally from the ultrasonic transducer, the proximal body portion defining a longitudinal axis;

a distal body portion defining a blade;
a plurality of spheres of material arranged in a series, the plurality of spheres of material extending between and interconnecting the proximal body portion and the distal body portion, wherein at least one sphere of material of the plurality of spheres of material is configured to articulate relative to at least one other sphere of material of the plurality of spheres of material to thereby articulate the distal body portion from an aligned orientation on the longitudinal axis to an articulated orientation angled off the longitudinal axis; and
a flexible sleeve disposed about the plurality of spheres of material and configured to maintain longitudinal compression of the plurality of spheres, abutment of a proximal-most sphere of material of the plurality of spheres of material with a solid distal end of the proximal body portion, and abutment of a distal-most sphere of material of the plurality of spheres of material with a solid proximal end of the distal body portion.

2. The ultrasonic surgical instrument according to claim 1, wherein the flexible sleeve is configured to maintain the plurality of spheres of material in the series with each sphere of material in contact with any adjacent spheres of material.

3. The ultrasonic surgical instrument according to claim 2, wherein the flexible sleeve extends proximally to be disposed about a portion of the proximal body portion and distally to be disposed about a portion of the distal body portion.

4. The ultrasonic surgical instrument according to claim 1, wherein in the articulated orientation, the distal body portion is disposed at an angle of about 45 degrees to about 90 degrees relative to the longitudinal axis.

5. The ultrasonic surgical instrument according to claim 1, further comprising:
an elongated shaft surrounding at least a portion of the proximal body portion of the ultrasonic waveguide;
a support shaft surrounding at least a portion of the distal body portion of the ultrasonic waveguide; and
an articulating section extending between and interconnecting the elongated shaft and the support shaft, wherein the plurality of spheres of material extend through the articulating section.

6. The ultrasonic surgical instrument according to claim 5, further comprising:
a jaw pivotably coupled to the support shaft and configured to pivot relative to the blade between an open position and a clamping position to enable clamping of tissue between the jaw and the blade.

7. The ultrasonic surgical instrument according to claim 5, further comprising a handle assembly, wherein the elongated shaft and proximal body portion of the ultrasonic waveguide extend distally from the handle assembly, and wherein the handle assembly supports the ultrasonic transducer thereon.

8. The ultrasonic surgical instrument according to claim 5, further comprising a robotic arm of a robotic surgical system, wherein the elongated shaft and proximal body portion of the ultrasonic waveguide extend distally from the robotic arm, and wherein the robotic arm supports the ultrasonic transducer thereon.

9. The ultrasonic surgical instrument according to claim 1, wherein at least one sphere of material of the plurality of spheres of material is configured to articulate in a first direction and wherein at least one sphere of material of the plurality of spheres of material is configured to articulate in a second direction perpendicular to the first direction.

10. A surgical ultrasonic waveguide assembly, comprising:

a proximal body portion configured to connect to an ultrasonic transducer, the proximal body portion defining a longitudinal axis;

a distal body portion defining a blade;

a plurality of spheres of material arranged in a series, the plurality of spheres of material extending between and interconnecting the proximal body portion and the distal body portion, wherein at least one sphere of material of the plurality of spheres of material is configured to articulate relative to at least one other sphere of material of the plurality of spheres of material to thereby articulate the distal body portion from an aligned orientation on the longitudinal axis to an articulated orientation angled off the longitudinal axis; and a flexible sleeve disposed about the plurality of spheres of material and configured to maintain the plurality of spheres of material in the series with each sphere of material in contact with any adjacent spheres of material and to maintain abutment of a proximal-most sphere of material of the plurality of spheres of material with a solid distal end of the proximal body portion.

11. The surgical ultrasonic waveguide assembly according to claim 10, wherein the proximal body portion is a solid rod of material.

12. The surgical ultrasonic waveguide assembly according to claim 10, wherein the distal body portion is a solid rod of material.

13. The surgical ultrasonic waveguide assembly according to claim 10, wherein each of the spheres of material is a solid sphere of material.

14. The surgical ultrasonic waveguide assembly according to claim 10, wherein each of the spheres of material is formed from stainless steel.

15. The surgical ultrasonic waveguide assembly according to claim 10, wherein the blade is curved in at least one direction.

16. The surgical ultrasonic waveguide assembly according to claim 10, wherein the blade is tapered in at least one dimension in a proximal-to-distal direction.

17. The surgical ultrasonic waveguide assembly according to claim 10, wherein the flexible sleeve is further configured to maintain the plurality of spheres of material under compression.

18. The surgical ultrasonic waveguide assembly according to claim 10, wherein the flexible sleeve extends proximally to be disposed about a portion of the proximal body portion and distally to be disposed about a portion of the distal body portion.

19. The surgical ultrasonic waveguide assembly according to claim 10, wherein in the articulated orientation, the distal body portion is disposed at an angle of about 45 degrees to about 90 degrees relative to the longitudinal axis.

* * * * *